US012343167B2

(12) United States Patent
Shimuta et al.

(10) Patent No.: US 12,343,167 B2
(45) Date of Patent: Jul. 1, 2025

(54) MEASURING DEVICE WITH WRINKLE SUPPRESSION

(71) Applicant: Murata Manufacturing Co., Ltd., Nagaokakyo (JP)

(72) Inventors: Toru Shimuta, Nagaokakyo (JP); Jun Takagi, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 1078 days.

(21) Appl. No.: 17/318,355

(22) Filed: May 12, 2021

(65) Prior Publication Data
US 2021/0259631 A1 Aug. 26, 2021

Related U.S. Application Data

(63) Continuation of application No. PCT/JP2020/004069, filed on Feb. 4, 2020.

(30) Foreign Application Priority Data

Feb. 4, 2019 (JP) ................. 2019-017731

(51) Int. Cl.
A61B 5/00 (2006.01)
A61B 5/026 (2006.01)
(Continued)

(52) U.S. Cl.
CPC .............. A61B 5/682 (2013.01); A61B 5/026 (2013.01); A61B 5/14507 (2013.01);
(Continued)

(58) Field of Classification Search
CPC .................................. A61B 5/682
See application file for complete search history.

(56) References Cited

U.S. PATENT DOCUMENTS 7,530,738 B2   5/2009 Price
8,123,401 B2   2/2012 Price
(Continued)

FOREIGN PATENT DOCUMENTS

JP   2007301356 A   11/2007
JP   2010230538 A   10/2010
(Continued)

OTHER PUBLICATIONS

Written Opinion of the International Search Authority issued for CT/JP2020/004069, date of mailing Apr. 7, 2020.
(Continued)

Primary Examiner — Puya Agahi
(74) Attorney, Agent, or Firm — ArentFox Schiff LLP

(57) ABSTRACT

A measuring device is provided that suppresses wrinkle generation. The measuring device includes a body and a cover to be attached to the body. The body includes a grip and also includes a sensor portion. A fixation portion is formed at an upper surface of the grip. The sensor portion includes a measuring portion disposed at a distal end thereof and a connection portion that connects between the measuring portion and the grip. A sensor is disposed in the measuring portion. In the measuring device, an angle between (1) a reference plane comprising the measurement surface and (2) a tangent line drawn between the fixation portion and the body as viewed in a direction that is perpendicular to the longitudinal direction and that is parallel to the reference plane, is 50 degrees or less.

1 Claim, 9 Drawing Sheets

(51) Int. Cl.
*A61B 5/145* (2006.01)
*A61B 5/1477* (2006.01)

(52) U.S. Cl.
CPC ...... *A61B 5/14539* (2013.01); *A61B 5/14542* (2013.01); *A61B 5/14546* (2013.01); *A61B 5/1477* (2013.01); *A61B 5/4875* (2013.01); *A61B 2560/0425* (2013.01)

(56) References Cited

U.S. PATENT DOCUMENTS

2008/0089387 A1    4/2008   Price
2009/0185598 A1    7/2009   Price

FOREIGN PATENT DOCUMENTS

| | | | | |
|---|---|---|---|---|
| JP | 2018186880 A | 11/2018 | | |
| WO | WO-2004028359 A1 * | 4/2004 | ............... | A61B 5/00 |
| WO | 2013018295 A1 | 2/2013 | | |
| WO | 2014041585 A1 | 3/2014 | | |

OTHER PUBLICATIONS

International Search Report issued for PCT/JP2020/004069, date of mailing Apr. 7, 2020.

* cited by examiner

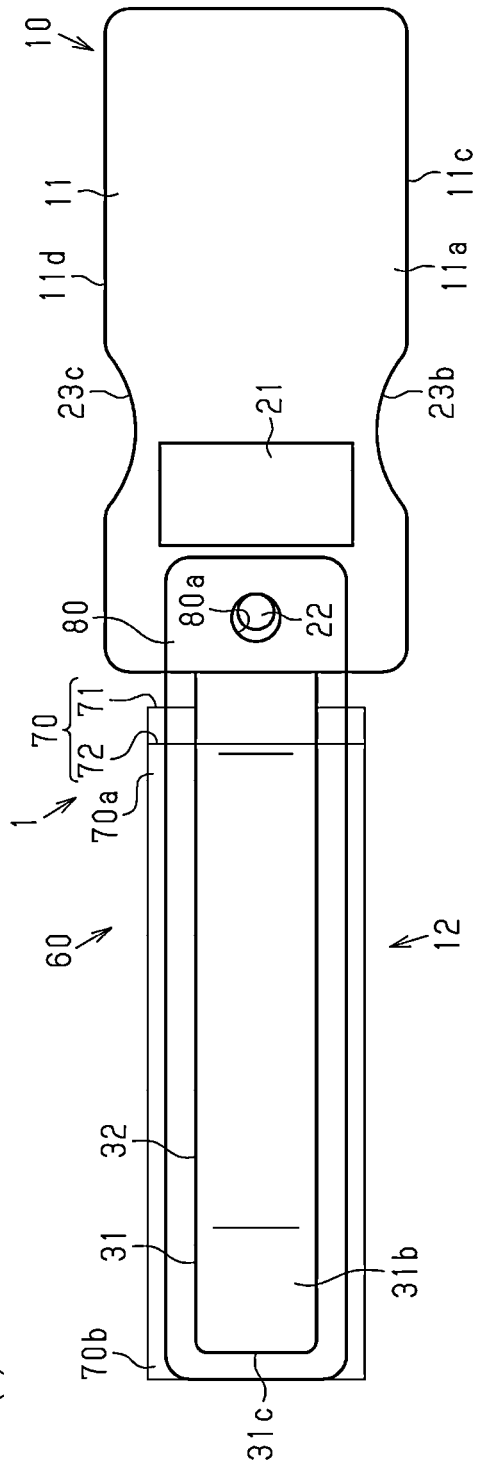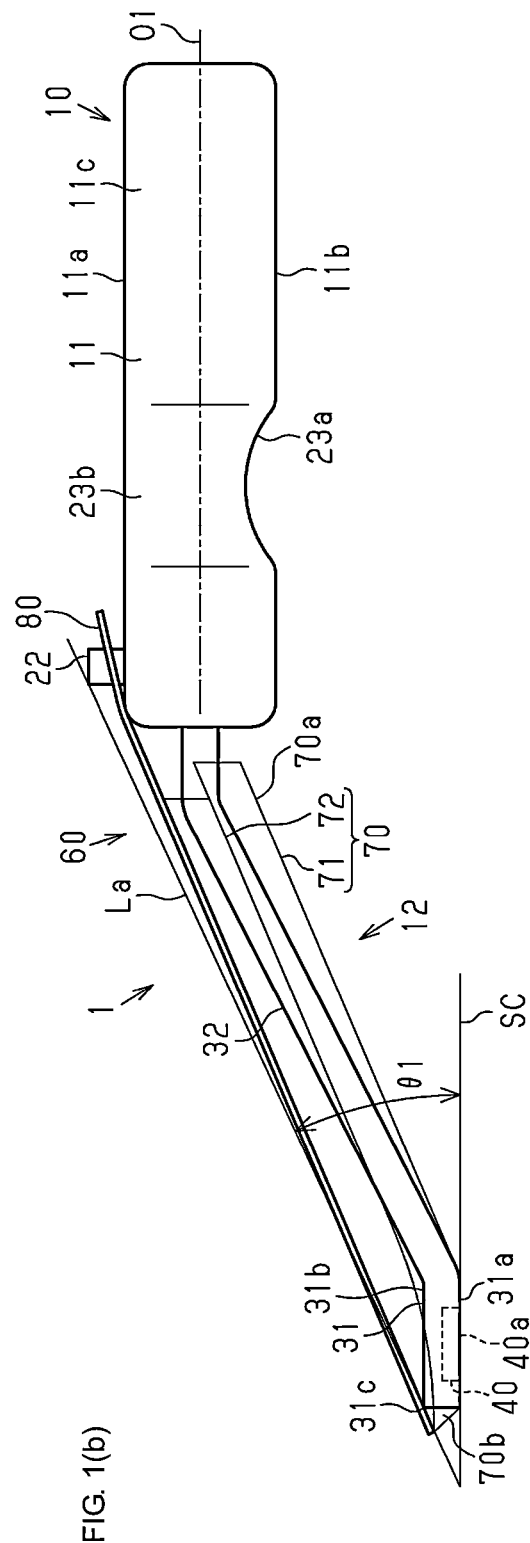
FIG. 1(a)
FIG. 1(b)

MEASURING DEVICE WITH WRINKLE SUPPRESSION

CROSS-REFERENCE TO RELATED APPLICATIONS

The present application is a continuation of International application No. PCT/JP2020/004069, filed Feb. 4, 2020, which claims priority to Japanese Application No. 2019-017731, filed on Feb. 4, 2019, the entire contents of each of which are incorporated herein by reference.

TECHNICAL FIELD

The present disclosure relates to a measuring device that suppresses wrinkle generation.

BACKGROUND

An oral moisture measuring device is a known example of a measuring device configured to be held by hand when measuring an object. For example, International Patent Publication No. 2004/028359 (hereinafter Patent Document 1) describes an oral moisture measuring device that includes an electrical capacitance sensor and measures an amount of moisture of a measurement object (e.g., inside the oral cavity) with the sensor being in contact with the target surface of the measurement object.

The cover thickness of the measurement surface of the sensor, as described in Patent Document 1, is "thin" so as not to affect the measurement sensitivity. The thin cover, however, is vulnerable to wrinkle generation at the measurement surface of the sensor depending on fitting conditions of the cover. This wrinkle generation affects measurement results of the oral moisture measuring device and can lead to inaccurate measurements.

SUMMARY

Aspects of the present disclosure are directed to addressing this shortcoming, namely, wrinkle generation.

A measuring device according to an aspect of the present disclosure includes a body in which a sensor portion and a grip are disposed in a longitudinal direction of the body, in which a sensor is disposed at an end portion of the sensor portion, the end portion being positioned opposite to the grip, and in which a measurement surface of the sensor is exposed from the sensor portion. In the measuring device, a fixation portion that a cover for covering the sensor is fixed to is disposed at a surface of the body that is opposite to the surface at which the measurement surface is exposed. In addition, when a reference plane is defined so as to include the measurement surface and when a tangent line is drawn so as to come into contact with the fixation portion and the body as viewed in a direction that is perpendicular to the longitudinal direction and that is parallel to the reference plane, an angle between the tangent line and the reference plane is 50 degrees or less. With this configuration, wrinkle generation in the cover that covers the sensor can be reduced, and thus the measuring device suppresses wrinkle generation.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

FIG. 1(*a*) is a plan view illustrating a measuring device.
FIG. 1(*b*) is a side view illustrating the measuring device.
FIG. 3(*b*) is a side view illustrating the support member and the fixation portion.
FIG. 4(*b*) is a side view illustrating the support member and fixation portion of the first modification example.
FIG. 10(*b*) is a side view illustrating the measuring device of the seventh modification example.
FIG. 11(*b*) is a side view illustrating the measuring device of the eight modification example.
FIG. 12(*b*) is a side view illustrating the measuring device of the ninth modification example.
FIG. 13(*b*) is a side view illustrating the measuring device of the tenth modification example.

DETAILED DESCRIPTION

Figure 2:
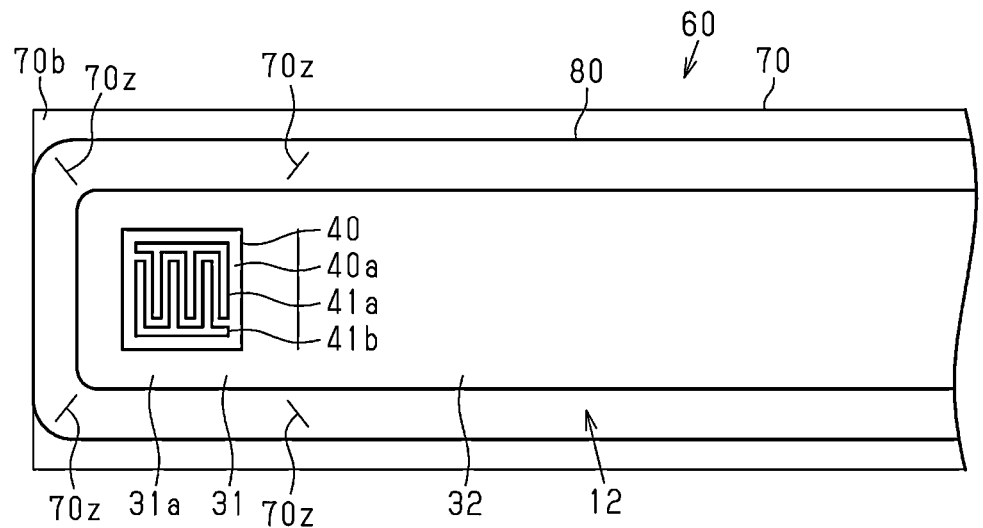
FIG. 2 is an enlarged view illustrating part of a sensor portion and of a cover.
Figure 3A:
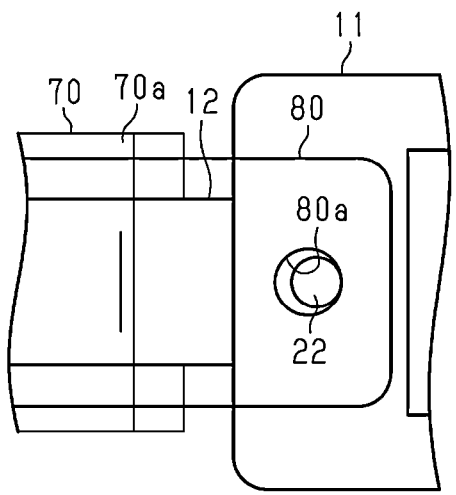
FIG. 3(*a*) is a plan view illustrating a support member and a fixation portion.
Figure 3B:
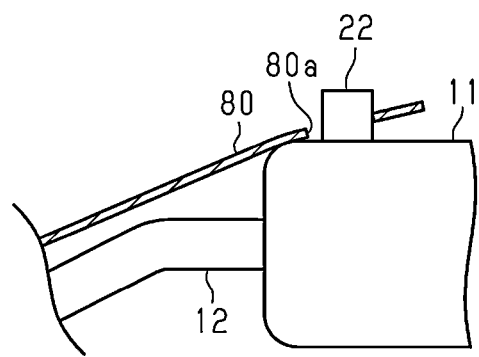

As illustrated in FIGS. 1(*a*) and 1(*b*), a measuring device 1 is, for example, an oral moisture measuring device for measuring the amount of moisture of a measurement object (i.e., an intraoral site). The measuring device 1 includes a body 10 and a cover 60 to be attached to the body 10.

As shown, the body 10 includes a grip 11 disposed in an end region of the body 10 in the longitudinal direction thereof and also includes a sensor portion 12 disposed in the other end region of the body 10.

The grip 11 is shaped generally like a cuboid having an upper surface 11*a*, a lower surface 11*b*, and side surfaces 11*c* and 11*d*. A display 21 and a fixation portion 22 are formed at the upper surface 11*a* of the grip 11. A recess 23*a* is formed at the lower surface 11*b* of the grip 11, and recesses 23*b* and 23*c* are formed at respective side surfaces 11*c* and 11d. The recesses 23a to 23c are formed so as to enable a user to place a finger therein when the user holds the measuring device 1. The recesses 23a to 23c enable the user to grip the grip 11 securely.

In the present embodiment, the sensor portion 12 extends in a direction opposite to the direction in which the grip 11 extends. The sensor portion 12 has a measuring portion 31 at a distal end thereof and a connection portion 32 that connects between the measuring portion 31 and the grip 11.

As illustrated in FIG. 1(a), the measuring portion 31 is shaped generally like a square plate. The distal end of the sensor portion 12 is an upper-end side 31c of the measuring portion 31. The side 31c is formed linearly. For example, the side 31c forms a straight line extending in a direction substantially perpendicular to a straight line connecting between the sensor portion 12 and the grip 11. Note that the side 31c may be formed so as to extend in a direction substantially perpendicular to an extending direction of a side surface of the connection portion 32. Moreover, the measuring portion 31 may have a rectangular or trapezoidal shape as viewed in a direction perpendicular to a first surface 31a. In the present embodiment, the measuring portion 31 has arcuate corners.

As illustrated in FIG. 2, a sensor 40 is disposed in the measuring portion 31. The sensor 40 is shaped like a tabular plate. The sensor 40 has a flat measurement surface 40a. For example, the sensor 40 is an electrical capacitance sensor. A pair of electrodes 41a and 41b are formed on the measurement surface 40a of the sensor 40. For example, the pair of electrodes 41a and 41b are disposed inter-digitally.

The pair of electrodes 41a and 41b serve as electrodes of a capacitor. More specifically, the measurement surface 40a opposes a measurement object, and the measurement object and a liquid that covers the object serve as dielectrics for the pair of electrodes 41a and 41b. The capacitance of the pair of electrodes 41a and 41b corresponds to the amount of water in the measurement object and on the surface thereof.

In the exemplary aspect, the measuring device 1 includes a circuit board (not illustrated) on which components, such as an oscillation circuit and a control circuit, are mounted. The oscillation circuit outputs a signal with a frequency corresponding to the capacitance of the sensor. The control circuit detects the amount of water of the measurement object on the basis of the number of pulses of the output signal of the oscillation circuit. The control circuit displays the detected amount of water on the display 21.

As illustrated in FIG. 1(b), the measuring portion 31 has a second surface 31b that faces in a direction opposite to the facing direction of the measurement surface 40a of the sensor 40. The second surface 31b and the first surface 31a of the measuring portion 31 and the measurement surface 40a are formed so as to be parallel to each other. The connection portion 32 is shaped generally like a rectangular plate. The sensor portion 12 is bent so as to form a predetermined angle between the measuring portion 31 and the connection portion 32.

As described above, the grip 11 is shaped generally like a cuboid having the upper surface 11a, the lower surface 11b, and the side surfaces 11c and 11d. At least one of the longitudinal axis O1, the upper surface 11a, and the lower surface 11b of the grip 11 extends parallel to the first surface 31a of the measuring portion 31, in other words, parallel to the measurement surface 40a of the sensor 40.

A cover 60 includes a cover member 70 and a support member 80. In the present embodiment, the cover member 70 is shaped like a rectangular bag. The cover member 70 is preferably transparent or translucent. The cover 60 is attached to the body 10 such that the cover member 70 covers the measuring portion 31 positioned at the distal end of the sensor portion 12.

In the present embodiment, the cover member 70 is formed of a first cover sheet 71 and a second cover sheet 72 connected to the first cover sheet 71 at respective sides. Accordingly, the first cover sheet 71 and the second cover sheet 72 form a flat bag without gussets. For example, the first cover sheet 71 and the second cover sheet 72 may be welded to each other. A side of the cover member 70 at which the first cover sheet 71 and the second cover sheet 72 are not welded is referred to as an opening end 70a, whereas the distal end of the cover member 70 (i.e., the side of the cover member 70 opposite to the opening end) is referred to as a mouth-insertion end 70b. Note that the cover member 70 may be formed into a bag, for example, by folding a single cover sheet into two leaves and connecting the leaves together. Alternatively, the cover member 70 may be formed using an adhesive, a double-sided adhesive tapes, or the like.

For example, the material of the cover member 70 may be a resin having hydrophobic properties. The resin may be a thermoplastic resin. The resin having such properties may be, for example, polyethylene (PE), polypropylene (PP), polyethylene terephthalate (PET), nylon, polyvinyl chloride, and polyimide according to exemplary aspects.

The thickness of the cover member 70 is set so as to enable the sensor 40 to measure and so as not to disturb the measurement. For example, the thickness of the cover member 70 may be 5 µm or more and 30 µm or less, and preferably 5 µm or more and 15 µm or less. Note that the thickness of the cover member 70 may be adjusted appropriately in accordance with the material of the cover member 70. If the thickness of the cover member 70 exceeds 30 µm, the sensitivity of the sensor 40 drops considerably.

The cover member 70 is connected to the support member 80 using a connection member (not illustrated). For example, the connection member is an acrylic- or silicon-based adhesive, a double-sided adhesive tape, or the like. The connection member is preferably transparent or translucent.

In the present embodiment, the support member 80 is shaped like a rectangular plate. The support member 80 has a width larger than the width of the measuring portion 31. As illustrated in FIGS. 1(a) and 1(b), the support member 80 extends from the mouth-insertion end 70b to the opening end 70a of the cover member 70. In addition, the support member 80 is longer than the cover member 70 and protrudes from the opening end 70a of the cover member 70. A through-hole 80a is formed in the support member 80 at a position outside the cover member 70. The through-hole 80a penetrates the support member 80 in the thickness direction. The through-hole 80a serves as an engagement portion for fixing the cover member 70 to the body 10. Thus, the through-hole 80a is used to fix the cover 60 to the grip 11. The support member 80 is preferably transparent or translucent.

The support member 80 is a rigid member. The material of the support member 80 may be higher in flexural modulus of elasticity and also in flexural strength than that of the cover member 70. For example, the material of the support member 80 may be a resin, such as PET, ABS, polycarbonate, acrylic, and PP.

For example, the thickness of the support member 80 is 50 µm or more and 300 µm or less. Note that the thickness of the support member 80 may be set in accordance with the material to be used. For example, in the case of the material of the support member 80 being the same as that of the cover member 70, the thickness of the support member 80 is preferably two or more to twenty or less times greater, more preferably five or more times greater, than the thickness of the cover member 70. Note that the thickness of the cover member 70 may be measured at the thickest portion or at the thinnest portion of the cover member 70. Alternatively, the thickness of the cover member 70 may be an average of thicknesses of the thickest portion and the thinnest portion of the cover member 70.

As illustrated in FIGS. 1(a), 1(b), 3(a), and 3(b), the cover 60 is attached to the grip 11 by inserting the fixation portion 22 of the grip 11 into the through-hole 80a of the support member 80. The cover 60 is detached from the body 10 by taking the support member 80 off the fixation portion 22. In other words, the fixation portion 22 and the through-hole 80a of the support member 80 enable the cover 60 to be attached to and detached from the grip 11.

In the present embodiment, as illustrated in FIG. 1(b), a plane containing the measurement surface 40a at the measuring portion 31 is referred to as a reference plane SC. For purposes of this disclosure, a tangent line La is drawn such that the line La comes into contact with the fixation portion 22 and with the side 31c of the measuring portion 31 of the body 10 as viewed in a direction that is perpendicular to the longitudinal direction of the body 10 and is parallel to the reference plane SC. Here, as described above, the fixation portion 22 is formed on the upper surface 11a of the grip 11 in the present embodiment. In other words, the fixation portion 22 is disposed on the surface of the body 10 that faces oppositely to the facing direction of the surface at which the measurement surface 40a is formed. Accordingly, the tangent line La is drawn at the side of the upper surface 11a of the grip 11 of the body 10. In this case, the angle θ1 formed between the tangent line La and the reference plane SC is set to be 50 degrees or less.

According to the exemplary aspect, the measuring device 1 includes the body 10 and the cover 60 to be attached to the body 10. The body 10 includes the grip 11 disposed in one longitudinal end region of the body 10 and the sensor portion 12 disposed in the other longitudinal end region of the body 10. The sensor portion 12 includes the measuring portion 31 at the distal end thereof and the connection portion 32 that connects between the measuring portion 31 and the grip 11. The sensor 40 is disposed in the measuring portion 31. The sensor portion 12 has such a shape that a bend is formed between the measuring portion 31 and the connection portion 32. As viewed in a direction perpendicular to the longitudinal direction of the body 10 and parallel to the reference plane SC, the angle θ1 between the tangent line La and the reference plane SC is 50 degrees or less. The measuring portion 31 of the sensor portion 12 is covered by the cover 60 that is attached to the body 10. Here, when the cover 60 is hooked onto the fixation portion 22, a portion of the cover 60 that extends from the fixation portion 22 to the side 31c of the measuring portion 31 comes into alignment with the tangent line La or with a line having a smaller angle than that of the tangent line La with respect to the reference plane SC as viewed in a direction perpendicular to the longitudinal direction of the body 10 and parallel to the reference plane SC. Accordingly, the angle θ1 can be regarded as a maximum angle to be formed between the reference plane SC and the portion of the cover 60 that extends from the fixation portion 22 to the side 31c of the measuring portion 31.

Evaluation tests were performed to evaluate different bodies having different angles θ1 between the tangent line La and the reference plane SC. The angle θ1 differed in an increment of 10 degrees, in other words, 0 degrees, 10 degrees, ... up to 90 degrees. The cover 60 was attached to each body. It was determined by visual inspection weather wrinkles were generated in a portion of the cover 60 that was in contact with the first surface 31a of the measuring portion 31. The result was that wrinkle generation was not visually observed in the bodies having angles θ1 of 0 to 50 degrees whereas wrinkle generation was visually observed in the bodies having angles θ1 of 60 to 90 degrees.

In the body 10 according to the present embodiment, the angle θ1 between the tangent line La and the reference plane SC is 50 degrees or less. Accordingly, the cover member 70 of the present embodiment, which is formed as a flat bag, readily comes into close contact with the entire measurement surface 40a of the sensor 40 formed in the measuring portion 31. Thus, wrinkle generation is suppressed in the cover 60, or the cover member 70, at the measurement surface 40a of the sensor 40.

If the angle θ1 between the tangent line La and the reference plane SC is greater than 50 degrees, it becomes difficult for the flat bag-shaped cover member 70 to come into close contact with the entire measurement surface 40a. In this case, wrinkles are readily generated in the portion of the cover member 70 that covers the measurement surface 40a of the sensor 40.

The measuring portion 31 of the sensor portion 12 is shaped generally like a square plate. The sensor 40 is disposed in the measuring portion 31 so as to be exposed at the first surface 31a. In the measuring portion 31, the first surface 31a and the second surface 31b that faces opposite to the facing direction of the measurement surface 40a of the sensor 40 are disposed parallel to the measurement surface 40a of the sensor 40. Accordingly, a user brings the sensor portion 12 into contact with a measurement object in such a manner that the second surface 31b of the measuring portion 31 is positioned parallel to the target surface of the measurement object. As a result, the first surface 31a of the measuring portion 31 (i.e., the entire measurement surface 40a of the sensor 40) is brought into close contact with the target surface of the measurement object. Accordingly, the user can perform measurement while confirming the state of the measurement surface 40a of the sensor 40 by observing the second surface 31b of the measuring portion 31, which can reduce variation in measurement.

At least one of the longitudinal axis O1, the upper surface 11a, and the lower surface 11b of the grip 11 extends parallel to the first surface 31a of the measuring portion 31, in other words, parallel to the measurement surface 40a of the sensor 40. Accordingly, observing the grip 11 enables the user to bring the sensor portion 12 into contact with the measurement object in such a manner that the first surface 31a of the measuring portion 31 is positioned parallel to the target surface of the measurement object. Even when the second surface 31b of the measuring portion 31 cannot be visually observed while the measuring portion 31 is in the mouth, the user can easily identify the position of the first surface 31a of the measuring portion 31, in other words, the position of the measurement surface 40a of the sensor 40, and can bring the measurement surface 40a of the sensor 40 into contact with the target surface of the measurement object.

The display 21 for displaying measurement results is disposed at the upper surface 11a of the grip 11. Accordingly, the user can check the measurement results while confirming the contact state of the sensor 40 in contact with the measurement object by using the grip 11.

Moreover, the side 31c of the measuring portion 31 is formed linearly. The side 31c comes into contact with the second cover sheet 72 of the cover 60. The second cover sheet 72 is joined to the support member 80 of which the rigidity is greater than that of the first cover sheet 71 and of the second cover sheet 72. When the substantially rectangular cover member 70 is installed over the measuring portion 31, the support member 80 applies substantially uniform tensile forces to the cover member 70 that covers the measuring portion 31, which reduces wrinkle generation in the cover member 70 at the measurement surface 40a of the sensor 40. This eliminates the necessity of forming the cover member 70 into a three-dimensional shape.

The grip 11 has the fixation portion 22 formed at the upper surface 11a thereof, which is the surface facing opposite to the facing direction of the first surface 31a of the measuring portion 31 at which the sensor 40 is disposed. This configuration leads to easy installation of the cover 60 over the body 10. For example, if the fixation portion 22 were disposed at the lower surface 11b of the grip 11, the user would need to bring the lower surface 11b to face upward when fixing the support member 80 of the cover 60 to the fixation portion 22, which would take more time.

The fixation portion 22 for fixing the cover 60, however, is disposed at the upper surface 11a of the grip 11, which is the surface facing oppositely to the facing direction of the measuring portion 31 of the sensor 40 that is disposed at the measurement surface 40a of the sensor portion 12. Accordingly, the support member 80 fixed to the fixation portion 22 pulls the cover member 70 in a direction opposite to the facing direction of the measurement surface 40a of the sensor 40. Thus, the cover member 70 can be brought into close contact with the measurement surface 40a of the sensor 40.

In the present embodiment, the cover 60 can be attached to and detached from the grip 11 of the body 10.

When the cover 60 is attached to the body 10 with the cover member 70 covering the measurement surface 40a of the sensor 40, the support member 80 comes at the second surface 31b of the measuring portion 31, which is the surface opposite to the measurement surface 40a of the sensor 40. The rigidity of the support member 80 is greater than that of the cover member 70. Accordingly, the support member 80 pulls the cover member 70 toward the second surface 31b of the measuring portion 31. The tension force of the support member 80 acts substantially equally on the portions of the cover member 70 that cover the four sides of the quadrangular-shaped measuring portion 31, which thereby brings the cover member 70 into close contact with the measurement surface 40a of the sensor 40. Here, as illustrated in FIG. 2, wrinkles 70z are generated in the cover member 70 at positions outside the corners of the quadrangular measuring portion 31. Bringing the cover member 70 into close contact with the measurement surface 40a of the sensor 40 can suppress generation of wrinkles of the cover member 70 at the measurement surface 40a of the sensor 40.

In the present embodiment, the cover member 70 is a flat bag without gussets. The flat bag without gussets is beneficial in that the support member 80 can readily exert tension on the cover member 70. In addition, the flat bag without gussets can be manufactured easily by simply joining resin sheets together. Note that the cover member 70 may be formed into a bag having gussets.

During measurement, saliva adheres to the cover member 70, which may make it difficult to detach the thin cover member 70 from the measuring portion 31. In the present embodiment, however, the support member 80 extends from the mouth-insertion end 70b to the opening end 70a of the cover member 70. Accordingly, the cover member 70 can be separated easily from the measuring portion 31 after measurement by using the rigid support member 80, which makes it easier to remove the cover member 70.

The through-hole 80a is formed through the support member 80. The cover 60 can be attached easily to the body 10 by engaging the through-hole 80a with the fixation portion 22. The cover 60 can be detached from the body 10 easily by taking the through-hole 80a of the support member 80 off the fixation portion 22.

The through-hole 80a for fixation is formed at the rigid support member 80. When the cover 60 is attached to the body 10, the support member 80 does not stretch but pulls the cover member 70 so as to bring the cover member 70 into contact with the measuring portion 31.

According to the above-described embodiment, the following advantageous effects can be obtained.

(1) The measuring device 1 includes the body 10 and the cover 60 to be attached to the body 10. Moreover, the body 10 includes the grip 11 disposed in one end region of the body 10 in the longitudinal direction thereof and also includes the sensor portion 12 disposed in the other end region of the body 10. The sensor portion 12 includes the measuring portion 31 at the distal end thereof and the connection portion 32 that connects between the measuring portion 31 and the grip 11. The sensor 40 is disposed in the measuring portion 31. As viewed in a direction perpendicular to the longitudinal direction of the body 10 and parallel to the reference plane SC, the angle θ1 between the tangent line La and the reference plane SC is 50 degrees or less. The measuring portion 31 of the sensor portion 12 is covered by the cover 60 configured to be attached to the body 10.

In the cover 60, the angle θ1 between the tangent line La and the reference plane SC is 50 degrees or less. Accordingly, the cover member 70 of the present embodiment, which is formed as the flat bag, readily comes into close contact with the entire measurement surface 40a of the sensor 40 formed in the measuring portion 31. Thus, wrinkle generation is reduced in the cover 60, or the cover member 70, at the measurement surface 40a of the sensor 40.

(2) The measuring portion 31 of the sensor portion 12 is shaped generally like the square plate. Moreover, the sensor 40 is disposed in the measuring portion 31 so as to be exposed at the first surface 31a. In the measuring portion 31, the second surface 31b that faces oppositely to the facing direction of the measurement surface 40a of the sensor 40 is disposed so as to be parallel to the measurement surface 40a of the sensor 40. Accordingly, the user brings the sensor portion 12 into contact with a measurement object in such a manner that the second surface 31b of the measuring portion 31 is positioned parallel to the target surface of the measurement object. As a result, the first surface 31a of the measuring portion 31, in other words, the entire measurement surface 40a of the sensor 40, is brought into close contact with the target surface of the measurement object. Accordingly, the user can perform measurement while confirming the state of the measurement surface 40a by observing the second surface 31b of the measuring portion 31, which can reduce variation in measurement.

(3) The fixation portion 22 is formed at the upper surface 11a of the grip 11, which is the surface facing oppositely to the facing direction of the first surface 31a of the measuring portion 31 at which the sensor 40 is disposed. This configuration leads to easy installation of the cover 60 over the body 10.

(4) The fixation portion 22 for fixing the cover 60 is disposed at the upper surface 11a of the grip 11, and the upper surface 11a faces oppositely to the facing direction of the measurement surface 40a of the sensor 40 that is disposed at the measuring portion 31 of the sensor portion 12. Accordingly, the support member 80 fixed to the fixation portion 22 pulls the cover member 70 in a direction opposite to the direction in which the measurement surface 40a of the sensor 40 faces. Thus, the cover member 70 can be brought into close contact with the measurement surface 40a of the sensor 40.

(5) The measuring device 1 includes the body 10 and the cover 60 to be attached to the body 10. The body 10 has the sensor portion 12 having the measurement surface 40a of the sensor 40 at the distal end thereof and also has the grip 11 to which the sensor portion 12 is connected. The cover 60 includes the cover member 70 made of a resin and configured to cover the measurement surface of the sensor 40 and also includes the support member 80 that is disposed at least on the side of the sensor portion 12 opposite to the side on which the measurement surface 40a is disposed. The support member 80 is joined to the cover member 70. The support member 80 has a thickness greater than that of the cover member 70.

In the cover 60, the support member 80 pulls the cover member 70 in the direction opposite to the facing direction of the measurement surface 40a and thereby brings the cover member 70 into contact with the measurement surface 40a. Accordingly, generation of wrinkles of the cover member 70 can be suppressed at the measurement surface 40a.

(6) The support member 80 extends from the mouth-insertion end 70b to the opening end 70a of the cover member 70. Accordingly, the cover member 70 to which saliva is adhered can be separated easily from the measuring portion 31 after measurement by using the rigid support member 80, which makes it easier to remove the cover member 70.

(7) The through-hole 80a for fixation is formed through the rigid support member 80 that does not stretch when the cover 60 is attached to the body 10. Accordingly, the support member 80 can pull the cover member 70 and bring the cover member 70 into contact with the measuring portion 31.

(8) The upper-end side 31c of the measuring portion 31, which is the distal end of the sensor portion 12, is formed linearly, and the measuring portion 31 has arcuate corners. Wrinkles are not generated readily at the arcuate corners, which reduces wrinkle generation at the measurement surface 40a.

The above exemplary embodiment may be modified as described below.

In the above embodiment, the through-hole 80a is formed through the support member 80 of the cover 60, and the fixation portion 22 is inserted in the through-hole 80a. The engagement between the support member 80 and the fixation portion 22 fixes the cover 60 to the grip 11. However, the structure for engagement between the support member 80 and the fixation portion 22 may be changed appropriately. It is sufficient that the cover 60 can be hooked on and fixed to the fixation portion 22.

Figure 4A:
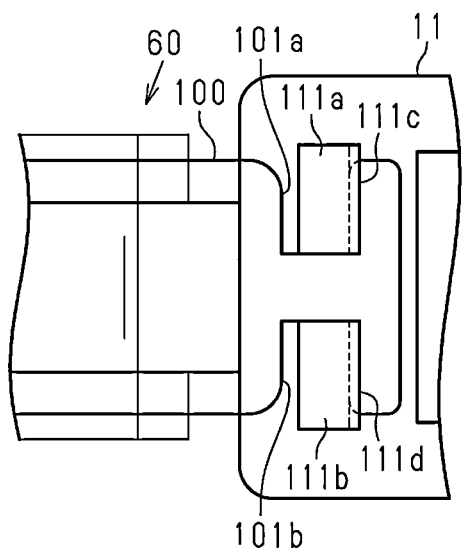
FIG. 4(*a*) is a plan view illustrating a support member and fixation portion of a first modification example.
Figure 4B:
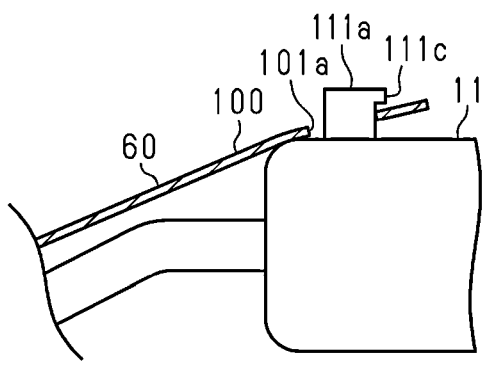

As illustrated in FIG. 4(a), slits 101a and 101b, which serve as the engagement portion, may be formed at a support member 100, and the slits 101a and 101b engage respective fixation portions 111a and 111b formed at the grip 11. The fixation portions 111a and 111b extend in directions perpendicular to the direction from the grip 11 toward the distal end of the sensor portion 12. As illustrated in FIGS. 4(a) and 4(b), locking portions 111c and 111d are formed at respective upper ends of the fixation portions 111a and 111b so as to protrude in a direction opposite to the distal end of the sensor portion 12. The locking portions 111c and 111d prevent the support member 80 from slipping off the fixation portion 22. Note that the locking portions 111c and 111d having such a shape may be formed at the fixation portion 22 of the above embodiment.

Figure 5:
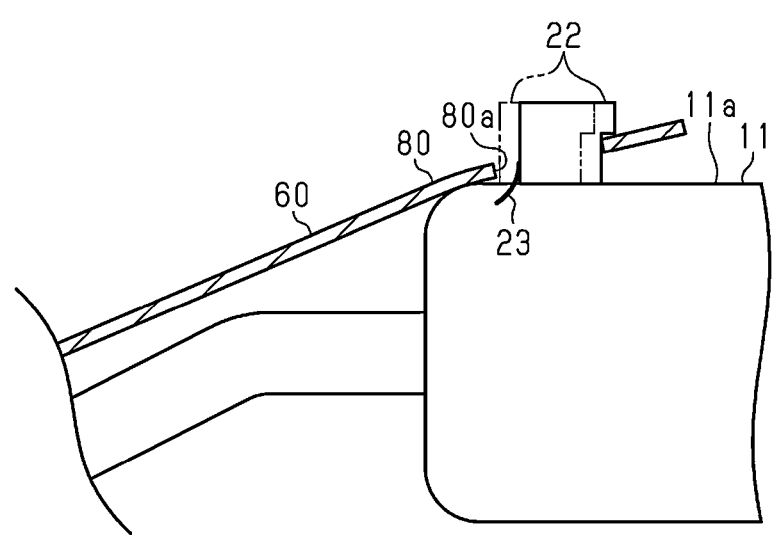
FIG. 5 is a side view illustrating a support member and fixation portion of a second modification example.

In the measuring device 1 illustrated in FIG. 5, an urging member 23 urges the fixation portion 22 in a direction opposite to the distal end of the sensor portion 12. For example, the urging member 23 may be a flat spring, a coil spring, or a rubber spring. The fixation portion 22 is supported at the grip 11 movably in the longitudinal direction of the body 10. The user moves the fixation portion 22 to the position indicated by the dash-dot-dot line in FIG. 5 and inserts the fixation portion 22 into the through-hole 80a of the support member 80 of the cover 60. The urging member 23 causes the fixation portion 22 to pull the cover member 70 via the support member 80 in a direction opposite to the distal end of the sensor portion 12 and to bring the cover member 70 into stable contact with the measurement surface 40a of the sensor 40 formed in the measuring portion 31 of the sensor portion 12. In the case of the fixation portion 22 being movable as described above, the angle θ1 is determined using a tangent line La that is drawn when the fixation portion 22 is at the position closest to the distal end of the sensor portion 12 in the example illustrated in FIG. 5. In this case, the angle θ1 between the tangent line La and the reference plane SC becomes largest.

Figure 6:
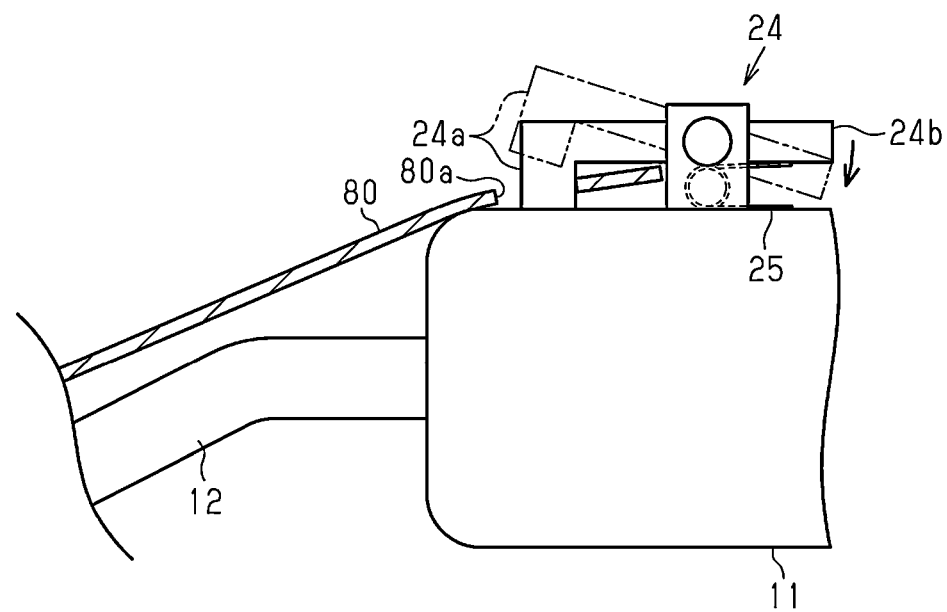
FIG. 6 is a side view illustrating a support member and fixation portion of a third modification example.

As illustrated in FIG. 6, the support member 80 of the cover 60 may be fixed to the grip 11 using a clip 24. The clip 24 is configured such that a locking portion 24a, which serves as the fixation portion, is urged toward the grip 11 by a spring 25. As a result of this configuration, the support member 80 can be easily fixed and removed by manipulating a manipulation portion 24b of the clip 24.

Figure 7:
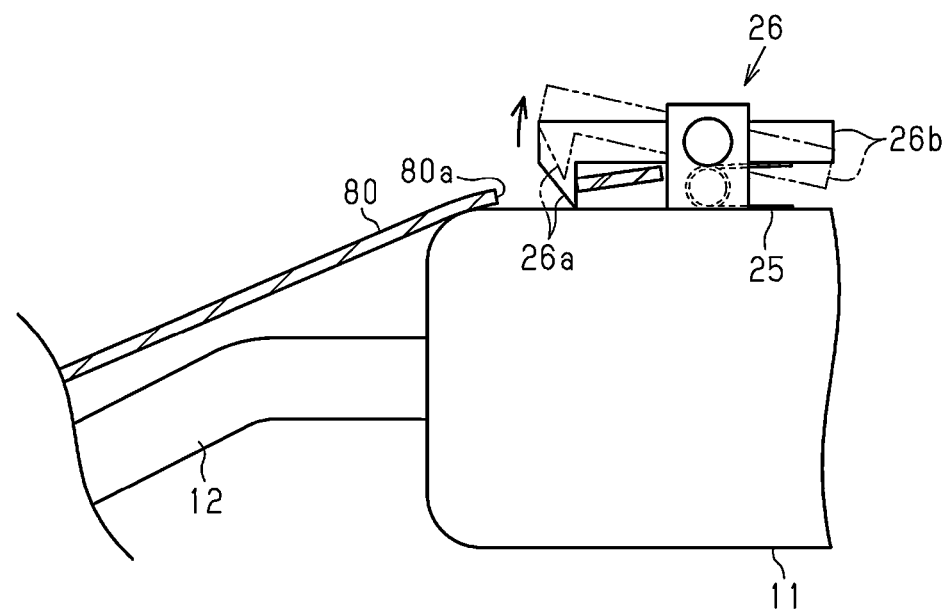
FIG. 7 is a side view illustrating a support member and fixation portion of a fourth modification example.

As illustrated in FIG. 7, a clip 26 can have a tapered locking portion 26a. This configuration enables the support member 80 to be inserted between the locking portion 26a and the grip 11 without manipulating the manipulation portion 26b of the clip 26. Accordingly, the cover 60 can be fixed easily.

In the above embodiment, the shape of the cover member 70 can be changed appropriately. For example, the cover member 70 may be shaped like a trapezoid in which the width of the cover member 70 becomes larger from the mouth-insertion end 70b toward the opening end 70a. As the size of the mouth-insertion end 70b becomes larger than the size of the measuring portion 31 of the sensor portion 12, it may become more difficult to bring the cover member 70 into close contact with the measurement surface 40a of the sensor 40 even if the support member 80 pulls the cover member 70. As a result, wrinkles are more likely to be generated. In this modification example, however, generation of the wrinkles can be suppressed since the size of the mouth-insertion end 70b does not become too large compared with the measuring portion 31 of the sensor portion 12. In addition, the mouth-insertion end 70b can be inserted easily into the oral cavity since the size of the mouth-insertion end 70b does not become too large compared with the measuring portion 31 of the sensor portion 12. Moreover, the sensor portion 12 can be inserted easily into the cover member 70 since the cover member 70 has a larger width at the opening end 70a than at the mouth-insertion end 70b.

Referring back to FIGS. 1(a) and 1(b), it is sufficient that as viewed in a direction perpendicular to the longitudinal direction of the body 10 and parallel to the reference plane SC, the fixation portion 22 is positioned, with respect to the longitudinal axis O1 of the grip 11, in a region of the body 10 that is opposite to a region in which the measurement surface 40a is exposed. In other words, it is sufficient that the fixation portion 22 is positioned in a region closer to the upper surface 11a. For example, the fixation portion 22 can be disposed at a corner portion between the upper surface 11a and a side surface 11c.

In the above embodiment, the fixation portion 22 is formed at the grip 11. The fixation portion 22, however, may be formed at the connection portion 32.

In the above embodiment, the bag-like cover may be formed by joining the support member 80 illustrated in FIGS. 1(a) and 1(b) to the first cover sheet 71. Alternatively, the bag-like cover may be formed by joining the support member 80 to the second cover sheet 72.

In the above embodiment, the support member 80 illustrated in FIGS. 1(a) and 1(b) may be formed by laminating multiple resin sheets. Moreover, at least one of the first cover sheet 71 and the second cover sheet 72 may be formed by laminating multiple resin sheets.

It should be appreciated that the shapes of the components in the above embodiment can be changed appropriately.

Figure 8:
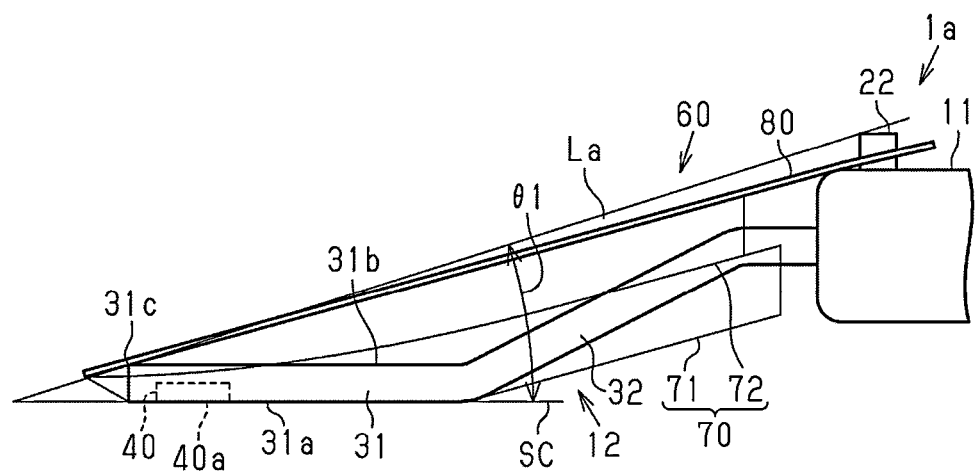
FIG. 8 is a side view illustrating part of a measuring device of a fifth modification example.
Figure 9:
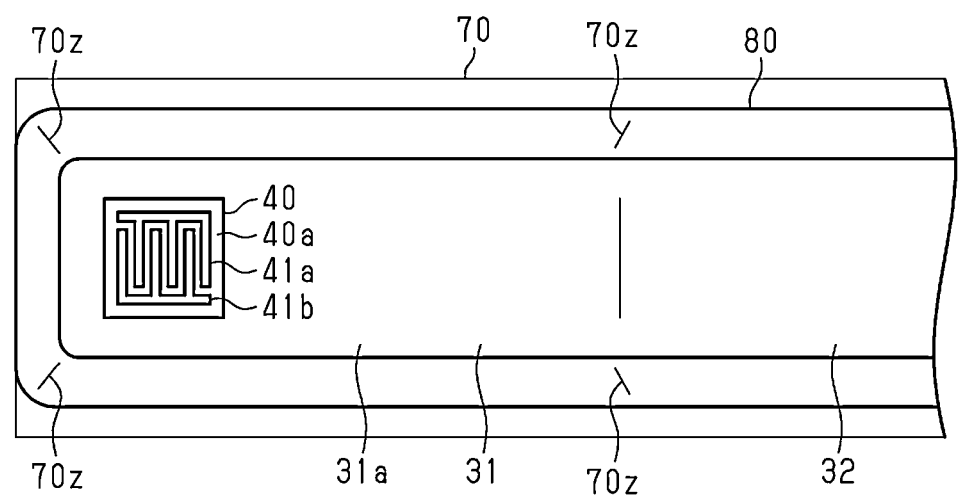
FIG. 9 is an enlarged view illustrating part of a sensor portion and of a cover of a sixth modification example.

In a measuring device 1a illustrated in FIGS. 8 and 9, the measuring portion 31 of the sensor portion 12 is shaped like an elongated rectangle. The measuring device 1a having this measuring portion 31 is beneficial in that the distal end of the sensor 40 can be inserted into the oral cavity easily. Using this sensor portion 12 and the same cover 60 as described in the above embodiment can suppress generation of wrinkles of the cover member 70 at the measurement surface 40a of the sensor 40 formed at the measuring portion 31.

The shape of the measuring device in the above embodiment may be changed appropriately. For example, as opposed to the above embodiment in which the sensor portion 12 includes the measuring portion 31 and the connection portion 32, the sensor portion 12 may have portions that are not clearly distinguishable.

Figure 10A:
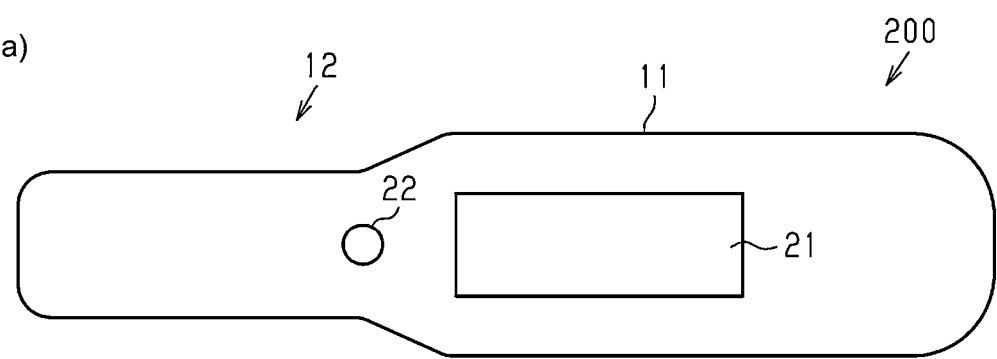
FIG. 10(*a*) is a plan view illustrating a measuring device of a seventh modification example.
Figure 10B:
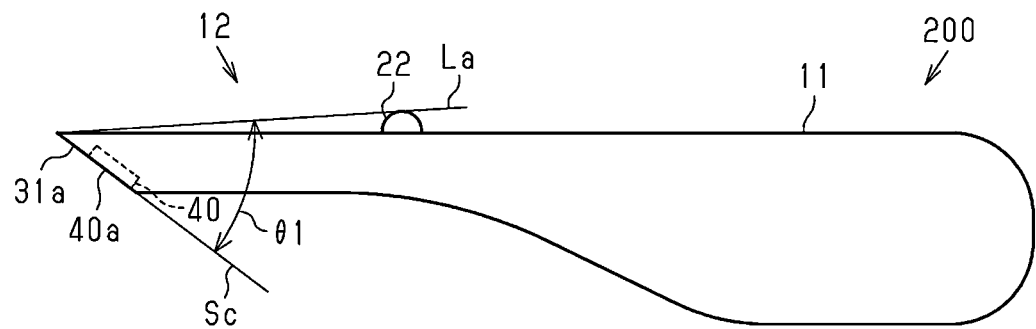

For example, as illustrated in FIGS. 10(a) and 10(b), a measuring device 200 has the sensor portion 12 and the grip 11 disposed in the longitudinal direction (in the right-left direction in FIG. 10(a)). As further shown the grip 11 has a columnar shape elongated in the longitudinal direction. In the cross section taken perpendicular to the longitudinal direction, the grip 11 may have such a shape as a polygon like a tetragon, a circle, an oval, or a combination of these, or a shape having arcuate corners. As illustrated in FIG. 10(b), the grip 11 is formed such that the vertical thickness becomes smaller toward the sensor portion 12. The entire sensor portion 12 is shaped substantially linearly, and the measurement surface 40a of the sensor 40 is inclined at a predetermined angle with respect to the extending direction of the sensor portion 12. Note that the fixation portion 22 of the measuring device 200 is formed in the sensor portion 12.

Figure 11A:
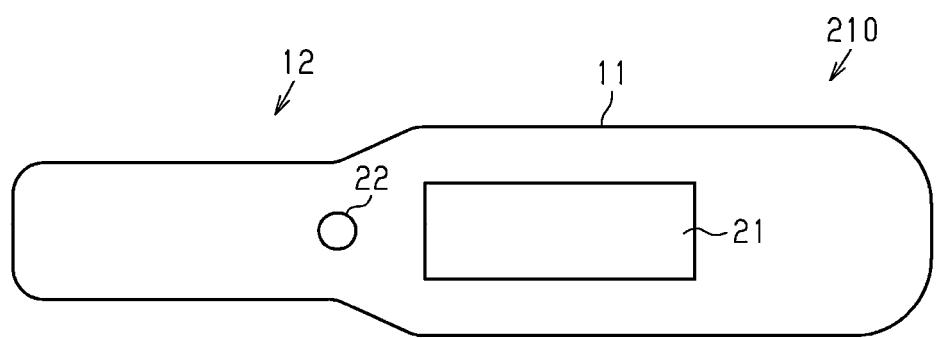
FIG. 11(*a*) is a plan view illustrating a measuring device of a eight modification example.
Figure 11B:
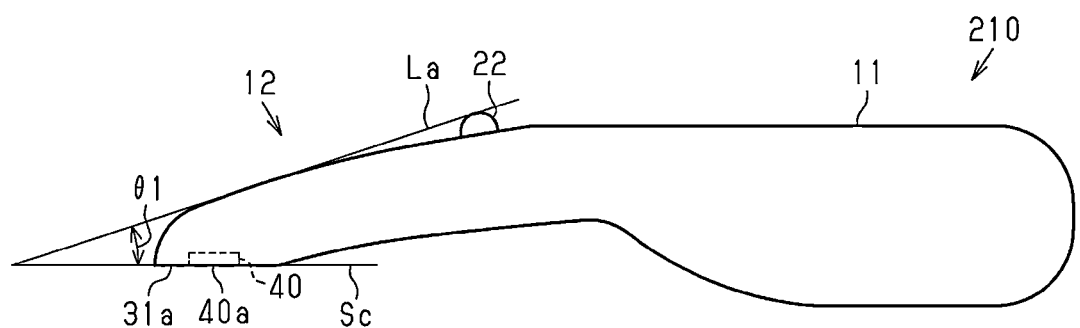

In addition, as opposed to the measuring device 200 illustrated in FIGS. 10(a) and 10(b), a measuring device 210 illustrated in FIGS. 11(a) and 11(b) has the sensor portion 12 that is generally bent. The sensor portion 12 is gradually bent downward toward the distal end thereof from the upper portion of the grip 11 at which the display 21 is formed.

Figure 12A:
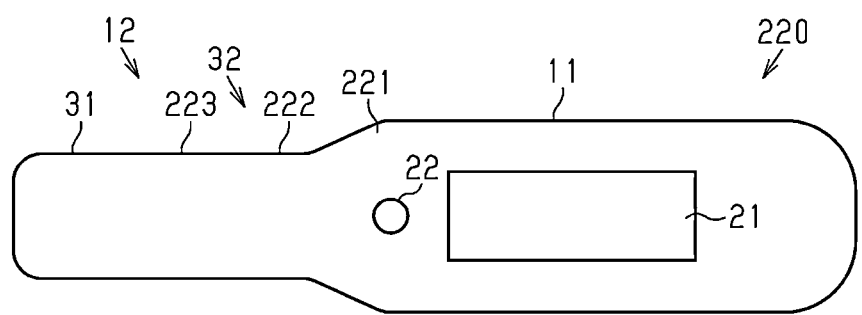
FIG. 12(*a*) is a plan view illustrating a measuring device of a ninth modification example.
Figure 12B:
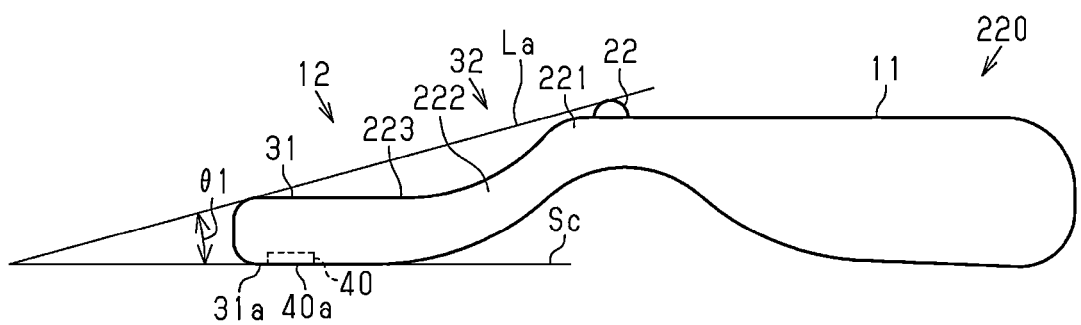

Moreover, the sensor portion 12 may be formed of three or more portions. As illustrated in FIGS. 12(a) and 12(b), a measuring device 220 includes a first portion 221 in which the connection portion 32 extends in the longitudinal direction from the upper portion of the grip 11, a second portion 222 extending obliquely downward from the distal end of the first portion 221, and a third portion 223 extending in the longitudinal direction from the distal end of the second portion 222. The sensor 40 is disposed at the end portion of the third portion 223. Note that a curved connection portion connects between the first portion 221 and the second portion 222 and also between the second portion 222 and the third portion 223.

Figure 13A:
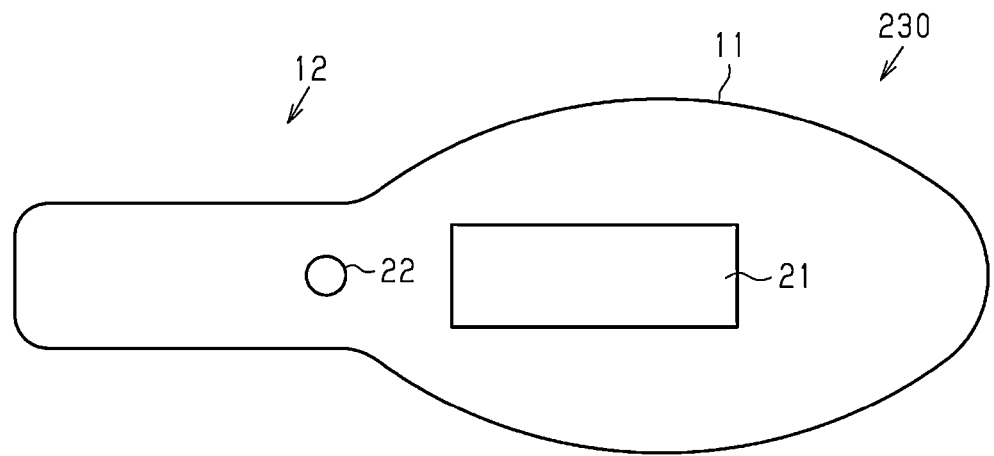
FIG. 13(*a*) is a plan view illustrating a measuring device of a tenth modification example.
Figure 13B:
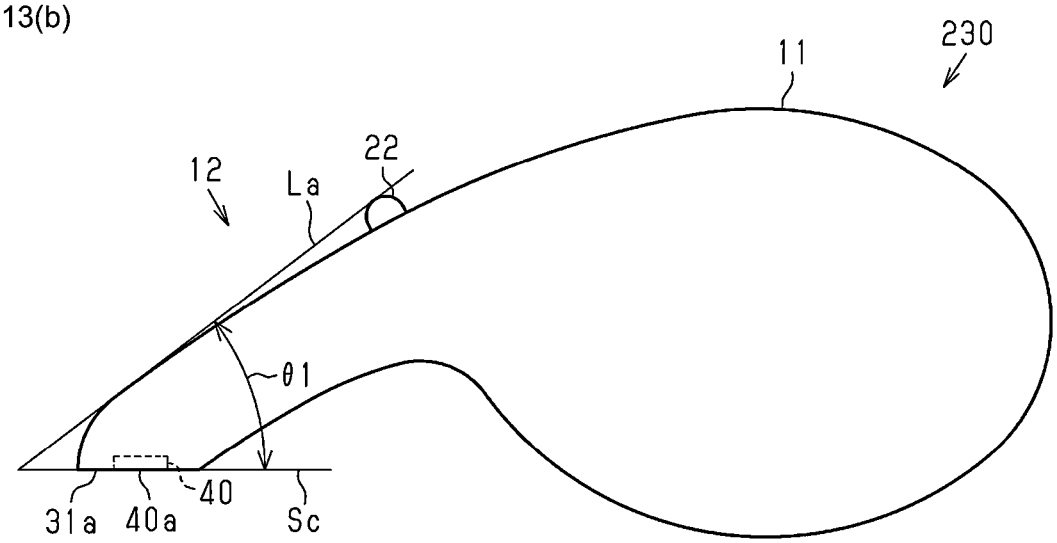

As illustrated in FIGS. 13(a) and 13(b), the grip 11 of a measuring device 230 is shaped like an ellipsoid elongated in the longitudinal direction, and the sensor portion 12 of the measuring device 230 is generally bent downward toward the distal end.

In the above exemplary embodiment, the measuring device 1 has been described as the device for measuring the amount of intraoral moisture. The measuring device 1, however, may be a device for measuring the amount of extraoral moisture.

In the above embodiment, the measuring device has been described as the device for measuring the amount of water. The measuring device, however, may be a device for measuring others. For example, the measuring device may be a pH measuring device or a device for measuring oral bacteria. The measuring device may be a device for measuring blood flow or blood oxygen. The measurement device may be a device for measuring multiple items. Accordingly, in such cases, it should be appreciated that the electrical capacitance sensor of the above embodiment is to be replaced with a sensor suitable for the measurement target.

The exemplary configurations described in the above embodiment and modification examples may be replaced partially with appropriate known configurations. The embodiment and modification examples described above may be partially or entirely combined with one another.

It is noted that the following technical idea can be derived from the above embodiment and modification examples.

A measuring device includes a body in which a sensor portion and a grip are disposed in a longitudinal direction of the body. In the body, the sensor portion has a measuring portion having a sensor of which a measurement surface is exposed at a first surface of the measuring portion, and the sensor portion also has a connection portion that connects between the measuring portion and the grip. The measuring device also includes a cover that covers at least the measuring portion. In the measuring device, the connection portion extends obliquely from the measuring portion and oppositely with respect to the first surface of the measuring portion facing. In addition, when a reference plane is defined so as to include the first surface of the measuring portion and when a first surface of the connection portion is positioned on a side of the body on which the reference plane and the first surface of the measuring portion is present, an angle between the first surface of the connection portion and the reference plane is 5 degrees or more and 50 degrees or less.

In general, it is noted that the exemplary embodiments of the present disclosure have been described above. The embodiments described above are for facilitating the understanding of the present disclosure, and are not intended to limit the present disclosure. The present disclosure can be modified or improved without departing from the gist thereof, and the present disclosure also includes equivalents thereof. In other words, modifications to the embodiments, which may be made by those skilled in the art as appropriate, are also included in the scope of the present disclosure as long as they have the features of the present disclosure. For example, the elements, the arrangement, the material, the condition, the shape, the size, and the like included in each embodiment are not limited to the examples described above, and may be appropriately changed. Furthermore, the elements included in each embodiment may be combined as technically possible, and the combinations thereof are also included in the scope of the present disclosure as long as they include the features of the present disclosure.

The invention claimed is:

1. A measuring device comprising:
   a body;
   a sensor portion and a grip disposed in a longitudinal direction of the body;
   a sensor disposed at an end portion of the sensor portion, the end portion being positioned opposite to the grip; and
   a measurement surface of the sensor exposed at the sensor portion,
   wherein a fixation portion, which a cover for covering the sensor is fixed to, is disposed at a surface of the body opposite to a surface thereof at which the measurement surface is exposed,
   wherein the cover comprises a cover member and a support member, and the cover is attached to the body such that the cover member covers a measuring portion positioned at a distal end of the sensor portion, the measuring portion including the measurement surface,
   wherein when the cover member is installed over the measuring portion, and the support member applies uniform tensile forces to the cover member that prevents wrinkle generation, and
   wherein an angle between a reference plane comprising the measurement surface and a tangent line drawn between the fixation portion and the body as viewed in a direction that is perpendicular to the longitudinal direction and that is parallel to the reference plane, is 50 degrees or less.

* * * * *